United States Patent
Zeng et al.

(10) Patent No.: US 6,576,759 B2
(45) Date of Patent: Jun. 10, 2003

(54) ANTISENSE INHIBITION OF RAD51

(75) Inventors: Hong Zeng, Cupertino, CA (US); Gurucharan Reddy, Redwood City, CA (US); Anne Vallerga, Menlo Park, CA (US); David A. Zarling, Menlo Park, CA (US)

(73) Assignee: Pangene Corporation, Fremont, CA (US)

( * ) Notice: Subject to any disclaimer, the term of this patent is extended or adjusted under 35 U.S.C. 154(b) by 0 days.

(21) Appl. No.: 09/454,495

(22) Filed: Dec. 6, 1999

(65) Prior Publication Data

US 2002/0147161 A1 Oct. 10, 2002

Related U.S. Application Data

(60) Provisional application No. 60/119,578, filed on Feb. 10, 1999.

(51) Int. Cl.[7] .......................... C07H 21/04; C12N 15/00
(52) U.S. Cl. ........................................ 536/24.5; 435/6
(58) Field of Search .......................... 435/6, 91.1, 91.3, 435/325, 375; 536/23.1, 23.2, 24.5, 24.3, 24.31, 24.33; 514/44

(56) References Cited

U.S. PATENT DOCUMENTS

| | | | | |
|---|---|---|---|---|
| 5,801,154 A | * | 9/1998 | Baracchini |
| 6,008,048 A | * | 12/1999 | Monia et al. |
| 6,037,125 A | | 3/2000 | Hasty |

FOREIGN PATENT DOCUMENTS

| | | |
|---|---|---|
| WO | 98/20030 | 5/1998 |
| WO | 98/34118 | 8/1998 |

OTHER PUBLICATIONS

Milner et al. "Selecting effective antisense reagents on combinatorial oligonucleotide arrays" Nature Biotechnology, vol. 15, pp. 537–541, Jun. 1997.*
Morita et al. "A mouse homolog of the *Escherichia coli* recA and *Saccharomyces crevisiae* RAD1 genes" PNAS, vol. 90, pp. 6577–6580, Jul. 1993.*
Branch, "A good antisense molecule is hard to find" Tibs23, p 45–50, Feb. 1998.*
Arawal, "Antisense oligonucleotides: towards clinical trials", TIBTech, vol. 14, pp. 376–387, Oct. 1996.*
Ohnishi, et al., "In vitro and in vivo potentiation of radiosensitivity of malignant gliomas by antisense inhibition of the Rad51 gene," *Biochem. Biophys. Res. Commun.* 245(2):319–324 (1998).
Haaf et al., "Nuclear foci of mammalian rad51 recombination protein in somatic cells after DNA damage and its localization in synaptonemal complexes," *Proc. Natl. Acad. Sci. USA,* 92:2298–2302 (1995).

Hays et al., "Complex formation in yeast double–strand break repair: Participation of rad51 rad52, rad55, and rad57 proteins," *Proc. Natl. Acad. Sci. USA,* 92:6925–6929 (1995).
Benson et al., Purification and Characterization of the human Rad51 protein, an analogue of *E. coli* RecA., *EMBO J.* 13:5764–5771 (1994).
Chanet et al., "Semidominant Mutations in the Yeast Rad51 Protein and Their Relationships with the Srs2 Helicase," *Molecular and Cellular Biology,* 16(9):4782–4789 (1996).
Sturzbecher et al., "p53 is linked directly to homologous recombination processes via RAD51/RecA protein interaction," *EMBO Journal,* 15(8):1992–2002 (1996).
Sharan et al., "Embryonic lethality and radiation hypersensitivity mediated by Rad51 in mice lacking Brca2," *Nature,* 386:804–810 (1997).
Hunter, "Cooperation between Oncogenes" *Cell* 64:249–270 (1991).
Scully et al., "Association of BRCA1 with Rad51 in mitotic and meiotic cells," *Cell* 88:265–275 (1997).
Vispe et al., "Mammalian Rad51 protein: A RecA homologue with pleiotropic functions," *Biochimie* 79:587–592 (1997).
Ogawa et al., "RecA–Like Recombination Proteins in Eukaryotes: Functions and Structures of Rad51 Genes," *Cold Spring Harbor Symposium on Quantitative Biology* 43:567–576 (1993).
McCluskie et al., "Route and Method of Delivery of DNA Vaccine Influence Immune Responses n Mice and Non–Human Primate," *Mollecular Medicine* 5:287–300 (1999).
Branch, "A good antisense molecule is hard to find," *TIBS* 23:45–50 (1998).
Flanagan et al., "Cellular penetration and antisense activity by a phenoxazine–substituted heptanucleotide," *Nature Biotech.* 17:48–52 (1999).
Crystal, "Transfer of Genes to Humans: Early Lessons and Obstacles to Success," *Science* 270:404–410 (1995).
Ellouze, et al., "Nucleotide Cofactor–Dependent Structural Change of *Xenopus laevis* Rad51 Protein Filament Detected by Small–Angle Neutron Scattering Measurements in Solution", *Biochemistry* 36:13524–13529 (1997).

(List continued on next page.)

*Primary Examiner*—Sean McGarry
*Assistant Examiner*—Karen A. Lacourciere
(74) *Attorney, Agent, or Firm*—Richard F. Trecarti; Dorsey & Whitney, LLP

(57) ABSTRACT

Provided herein are methods for inhibiting cell proliferation in an individual comprising administering to the individual a composition comprising a Rad51 inhibitor. Also provided herein is a method for inhibiting the growth of a cell comprising administering to said cell a composition comprising a Rad51 inhibitor. Such methods can further include the step of providing radiation or DNA damaging agents after administration of said Rad51 inhibitor. Also described herein are methods which are performed in vivo and/or on cancerous cells.

2 Claims, 10 Drawing Sheets

OTHER PUBLICATIONS

Morrison, et al., "The Essential Functions of Human Rad51 Are Independent of ATP Hydrolysis," *Mol. Cell. Biol.* 19(10):6891–6897 (1999).

Namsaraev and Berg, "Interaction of Rad51 with ATP and $Mg^{2+}$ Induces a Conformational Change in Rad51," *Biochemistry* 37:11932–11939 (1998).

Namsaraev and Berg, "Binding of Rad51p to DNA. Interaction of Rad51p With Single– and Double–stranding DNA," *Journal of Biological Chemistry* 273(11):6177–6182 (1998).

Zaitseva, et al., "The DNA Binding Properties of *Saccharomyces cerevisiae* Rad51 Protein," *Journal of Biological Chemistry* 274(5):2907–2915 (1999).

De Zutter and Knight, "The hRad51 and RecA Proteins Show Significant Differences in Cooperative Binding to Single–stranded DNA," *J. Mol. Biol.* 293:769–780 (1999).

Radding, "Helical interactions in homologous pairing and strand exchange driven by RecA protein," *J. Biol. Chem.* 266:5355–5358 (1991).

Kowalcyzkowski et al., "Homologous pairing and DNA strand–exchange proteins," *Annu. Rev. Biochem.* 63:991–1043 (1994).

Heyer, "The search for the right partner: homologous pairing and DNA strand exchange proteins in eukaryotes," *Experientia* 50(3):223–233 (1994).

Maeshima, et al., "RAD51 homologues in *Xenopus laevis*: two distinct genes are highly expressed in ovary and tests," *Gene* 160(2):195–200 (1995).

Ogawa, "Similarity of the yeast RAD51filament to the bacterial RecA filament," *Science* 259:1896–1899 (1993).

Story, "Structural relationship of bacterial RecA proteins to recombination proteins from bacteriophage T4 and yeast," *Science* 259:1892–1896 (1993).

Sung, "Catalysis of ATP–dependent homologous DNA pairing and strand exchange by yeast RAD51 proteins," *Science* 265:1241–1243 (1994).

Baumann, et al., "Human Rad51 protein promotes ATP–dependent homologous pairing and strand transfer reactions in vitro," *Cell* 87(4):757–766 (1996).

Gupta, et al., "Activities of human recombination protein Rad51," *Proc. Natl. Acad. Sci. USA* 94:463–468 (1997).

Game, "Radiation sensitive mutants and repair in yeast," in *Yeast Genetics: Fundamental and applied aspects.* Spencer and Smith, eds. Springer–Verlag, New York. pp. 109–137 (1983).

Haynes, et al., "DNA repair and mutagenesis in yeast," in *The molecular biology of the yeast Saccramomyces cerevisiae: life cycle and inheritance.* Strathern et al., eds. Cold Spring Harbor Laboratory Press, Cold Spring Harbor, New York. pp. 371–414 (1981).

Li et al., "Rad51 expression and localization in B cells carrying out class switch recombination," *Proc. Natl. Acad. Sci. USA* 93:10222–10227 (1996).

Ashley, et al., "Dynamic changes in Rad51 distribution on chromatin during meiosis in male and female vertebrates," *Chromosoma* 104:19–28 (1995).

Plug, et al., "Presynaptic association of Rad51 protein with selected sites in meiotic chromatin," *Proc. Natl. Acad. Sci. USA* 93:5920–5924 (1996).

Radding, in *Genetic Recombination,* Kucherlapati ed., American Society for Microbiology, Washington. pp. 193–230 (1988).

Tsuzuki, et al., "Targeted disruption of the Rad51 gene leads to lethality in embryonic mice," *Proc. Natl. Acad. Sci. USA* 93:6236–6240 (1996).

Lim, et al., "A Mutation in Mouse Rad51 Results in an Early Embryonic Lethal That Is Suppressed by a Mutation in p53," Molecular and Cellular Biology, 16(12):7133–7143 (1996).

Maldonado et al., "A human RNA polymerase II complex associated with SRB and DNA–repair proteins," *Nature* 381:86–89 (1996).

Buchhop, et al., "Interaction of p53 with the human Rad51 protein," *Nucleic Acids Research* 25(19):3868–3874 (1997).

Wooster, Localization of a breast cancer susceptibility gene, BRCA2, to chromosome 13q12–13, *Science* 265:2088–2090 (1994).

Smith et al., "Allele losses in the region 17q12–21 in familial breast and ovarian cancer involve the wild–type chromosome," *Nat Genet* 2:128–131 (1992).

Easton, et al., "Genetic linkage analysis in mailial breast and ovarian cancer: results from 214 families. The Breat Cancer Linkage Consortium." *Am. J. Hum. Genet.* 52:678–701 (1993).

Gayther et al., "Variation of risks of breast and ovarian cancer associated with different germline mutations of te BRCA2 gene," *Nat Genet* 15:103–105 (1997).

Albala, et al., "Identification of a novel human RAD51 homolog, RAD51B," *Genomics* 46(3):476–479 (1997).

Dosanjh, et al., "Isolation and characterization of RAD51C, a new human member of the RAD51 family of related genes," *Nucleic Acids Research* 26(5):1179–1184 (1998).

Pittman, et al., "Identification, characterization, and genetic mapping of Rad51d, a new mouse and human RAD51/RecA–related gene," *Genomics* 49(1):103–111 (1998).

Cartwright, et al., "The XRCC2 DNA repair gene from human and mouse encodes a novel member of the recA/RAD51 family," *Nucleic Acids Research* 26(13):3084–3089 (1998).

Liu, et al., "XRCC2 and XRCC3, new human Rad51–family members, promote chromosome stability and protect against DNA cross–links and other damages," *Mol Cell* 1(6):783–793 (1998).

Yuan, et al., "Regulation of Rad51 Function by c–Abl in Response to DNA Damage," *Journal of Biological Chemistry* 273(7):3799–3802 (1998).

Sonoda, et al., "Rad51–deficient vertebrate cells accumulate chromosomal breadks prior to cell death," *EMBO Journal* 17(2):598–608 (1998).

Shinohara, et al., "Cloning of human, mouse and fission yeast recombination genes homologous to RAD51 and recA," *Nat Genet* 4(3):239–243 (1993).

Huang, et al., "Role for caspase–mediated cleavage of Rad51 in induction of apoptosis by DNA damage," *Mol Cell Biol* 19(4):2986–2997 (1999).

Sung and Robberson, "DNA strand exchange mediated by a RAD51–ssDNA nucleoprotein filament with polarity opposite to that of RecA," *Cell* 82:453–461 (1995).

Haaf, et al., "Sequestration of Mammalian Rad51–Recombination Protein into Micronuclei," *J. Cell Biol* 144:11–20 (1999).

Raderschall, et al., "Nuclear foci of mammalian recombination proteins are located at located at single–stranded DNA regions formed after DNA damage," *Proc. Natl. Acad. Sci. USA* 96:1921–1926 (1999).

Golub, et al., "Interaction of human Rad51 recombination protein with single-stranded DNA binding protein, RPA" *Nucleic Acids Res.* 26:5388–5393 (1998).

Taki, et al., "Antisense inhibition of the RAD51 enhances radiosensitivity", *Biochem.Biophys.Res.Commun.* 223(2):434–438 (1996).

Roca and Cox, "The RecA protein: structure and function," *Crit. Rev. Biochem. Mol. Biol.,* 25(6):415–456 (1990).

Shinohara et al., "Rad51 protein involved in repair and recombination in *S. cerevisiae* is a Rec protein," *Cell,* 69(3):457–470 (1992).

Resnick, in *Meiosis,* (Moens, P.B., Ed.) pp. 157–210 Academic Press, New York (1987).

Friedberg, "Deoxyribonucleic acid repair in the yeast *Saccharomyces cerevisiae*", *Microbiol. Rev.,* 52(1):70–102 (1988).

Aboussekhra et al., "Semidominant suppressors of Srs2 helicase mutations of *Saccharomyces cerevisiae* map in the RAD51 gene, whose sequence predicts a protein with similarities to procaryotic RecA proteins," *Mol. Cell. Biol.* 12(7):3224–3234 (1992).

Basile et al., "Nucleotide sequences and transcriptional regulation of the yeast recombinational repair gene RAD51", *Mol. Cell. Biol.* 12(7):3235–3246 (1992).

Morita et al., "A mouse homolog of the *Escherichia coli* recA and *Saccharomyces cerevisiae* RAD51 genes," *Proc. Natl. Acad. Sci. USA* 90(14):6577–6580 (1993).

Kowalczykowski, "Biochemistry of genetic recombination: energetics and mechanism of DNA exchange," *Annu.. Rev. Biophys. Biophys. Chem.* 20:539–575 (1991).

Kowalczykowski et al., "Properties of the duplex DNA–dependent ATPase activity of *Escherichia coli* RecA and its role in branch migration," *Proc. Natl. Acad. Sci. USA* 84(10):3127–3131 (1987).

Kowalczykowski, et al., "Effects of the *Escherichia coli* SSB protein on the binding of *Escherichia coli* RecA protein to single-stranded DNA. Demonstration of competitive binding and the lack of a specific protein–protein interaction," *J. Mol. Biol.* 193(1):81–95 (1987).

Kowalczykowski, et al., "Effects of *Escherichia coli* SSB protein on the single-stranded DNA–dependent ATPase activity of *Escherichia coli* RecA protein. Evidence that SSB protein facilitates the binding of RecA protein to regions of secondary structure within single-stranded DNA", *J. Mol. Biol.* 193(1):97–113 (1987).

* cited by examiner

ACAACCAGATTGTATCTGAGGAAAGGAAGAGAGGGAAACCAGAGAATCTGCAAATCTACGACTCTCCCTGTC
TTCCTGAAGCTGAAGCTATGTTCGCCATTAATGCAGATGGAGTGGGAGATGCCAAAGACTGAATCATTGG
GTTTTCCCTCTGTTAAAACCTTAAGTGCTGCAGCCTAATGAGAGTGCACTGCTCCCTGGGGTTCTCTAC
AGGCCTCTCCTGTGTGACGTGCCAGGATAAAGCTTCCGGAAAACAGCTATTATATCAGCTTTTCTGAT
GGTATAAACAGGAGACAGGTCAGTAGTCACAAACTGATCTAAAATGTTTATTCCTTCTGTAGTGTATTAA
TCTCTGTGTGTTTCTTTGGTTTTGGAGAGGGTATGAAGTATCTTTGACATGGTGCCTTAGGAATGAC
TTGGGTTAACAAGCTGTCTACTGGACAATCTTATGTTTCCAAGAGAACTAAAGCTGAGAGACCTGACC
CTTCTCTCACTTCTAAATTAATGTAAATAAAATGCCTCAGTGCTATGTAGCAAAGGAATGGGTCTGCAC
AGATTCTTTTTTCTGTCAGTAAAACTCTCAAGCAGGTTTTAAGTTGTCTGTCTGAATGATCTGTGTA
AGGGTTTGGTTATGGAGTCTGTGCCAAACTAACTAGGCCATTAGCCCCTTCACCATCTACCTGCTTGGTC
TTTCATTGCTAAGACTAACTCAAGATAATCCTAGAGTCTTAAAGCATTCAGGCCAGTGTGGTCTTTGC
GCCTGTACTCCCAGCACTTTGGGAGGCCGAGGCAGGTGGATCGCTTGAGCCAGGAGTTTAAGTCCAGCT
TGGCCAAGATGGTGAAATCCCATCTCTACAAAAAATGCAGAACTTAATCTGGACACACTGTTACACGTGC
CTGTAGTCCCAGCTACTCTATAGCCTGAGGTGGGAGGAATCACTTAAGCCTGGAAGGTGGAAGTTGCAGTG
AGTCGAGATTGCACTGCTGCATTCCAGCCTGGGGTGACAGAGTGAGACCATGTTTCAAACAAGAAACATTT
CAGAGGGCAAGTAAACAGATTTGATTGTGAGGCTTCTAATAAAGTAGTAGTTATTAGTAGTG

CCGCGCGCAGCGGCCAGAGACCGAGCCCTAAGGAGAGTGCGGGCGCTTCCCGAGGCGTGCAGCTGGAACT
GCAACTCATCGGGTTGTGCGCAGAAGGCTGGGCAAGCGAGTAGAGAAGTGGAGCGTAAGCCAGGGGCG
TTGGGGGCCGTGCGGGTCGGGCGCGTGCCAGCGCCCGCGGGGTGAAGTCGGAGCGCGGGGCCTGCTGGAGA
GAGGAGCGCTGCCGACCGAGTAATGGCAATGCAGATGCAGCTTGAAGCAAATGCAGATACTTCAGTGGAA
GAAGAAAGCTTTGGCCCACAACCCATTTCACGTTAGAGCAGTGTGCATAAATGCCAACGATGTGAAGA
AATTGGAAGAAGCTGGATTCCATACTGTGGAGGCTGTTGCCTATGCGCCAAAGAAGGAGCTAATAAATAT
TAAGGGAATTAGTGAAGCCAAAGCTGATAAAATTCTGGCTCAGTCAGCAGCTAAATTAGTTCCAATGGGTTTC
ACCACTGCAACTGAATTCCACCAAAGGCGGTCAGAGATCATACAGATTACTACTGGCTCCAAAGAGCTTG
ACAAACTACTTCAAGGTGGAATTGAGACTGGATCTATCACAGAAATGTTTGGAGAATTCCGAACTGGGAA
GACCCAGATCGTCATACGCTAGCTGTCACCTGCCAGCTTCCCATTGACCGGGGTGGCAGTGCCTGAGAGGTATGGTC
GCCATGTACATTGACACTGAGGGTACCTTTAGGCCAGAACGGCTGCTGGCAGCGTTCAACACAGACCACCAGACCCAGCT
TCTCTGGCAGTGATGTCCTGGATAATGTAGCATATGCTCGAGCGTTCACTGCTTATTGTAGACAGTGCCACCGCC
CCTTTATCAAGCATCAGCCATGATGGTAGAATCTAGGTATGCACTTGGCCAGGCAGATGCACTTGGCCAGGTTTCTGC
CTTTACAGAACAGACTACTCGGGTCGAGGTGAGCTTTCAGCCAGGCAGATGCACTTGGCCAGGTTTCTGC
GGATGCTTCTGCCACTCGCTGATGAGTTTGGTGTAGCAGTGGTAATCACTAATCAGGTGGTAGCTCAAGT
GGATGGAGCAGCGATGTTTGCTGCTGATCCCAAAAAACCTATTGGAGGAAATATCATCGCCCATGCATCA

SEQUENCE LISTING

```
<160> NUMBER OF SEQ ID NOS: 10

<210> SEQ ID NO 1
<211> LENGTH: 2229
<212> TYPE: DNA
<213> ORGANISM: Homo sapiens

<400> SEQUENCE: 1
acaaccagat tgtatctgag gaaaggaaga ggggaaacca gaatctgcaa aatctacgac      60
tctccctgtc ttcctgaagc tgaagctatg ttcgccatta atgcagatgg agtgggagat     120
gccaaagact gaatcattgg gttttcctc tgttaaaaac cttaagtgct gcagcctaat     180
gagagtgcac tgctccctgg ggttctctac aggcctcttc ctgttgtgac tgccaggata     240
aagcttccgg gaaaacagct attatatcag cttttctgat ggtataaaca ggagacaggt     300
cagtagtcac aaactgatct aaaatgttta ttccttctgt agtgtattaa tctctgtgtg     360
```

-continued

```
ttttctttgg ttttggagga ggggtatgaa gtatctttga catggtgcct taggaatgac    420
ttgggtttaa caagctgtct actggacaat cttatgtttc caagagaact aaagctggag    480
agacctgacc cttctctcac ttctaaatta atggtaaaat aaaatgcctc agctatgtag    540
caaagggaat gggtctgcac agattctttt tttctgtcag taaaactctc aagcaggttt    600
ttaagttgtc tgtctgaatg atcttgtgta agggtttggt tatggagtct tgtgccaaac    660
ctactaggcc attagccctt caccatctac ctgcttggtc tttcattgct aagactaact    720
caagataatc ctagagtctt aaagcatttc aggccagtgt ggtgtcttgc gcctgtactc    780
ccagcacttt gggaggccga ggcaggtgga tcgcttgagc caggagtttt aagtccagct    840
tggccaagat ggtgaaatcc catctctaca aaaaatgcag aacttaatct ggacacactg    900
ttacacgtgc ctgtagtccc agctactcta tagcctgagg tgggagaatc acttaagcct    960
ggaaggtgga agttgcagtg agtcgagatt gcactgctgc attccagcca gggtgacaga    1020
gtgagaccat gtttcaaaca agaaacattt cagagggcaa gtaaacagat ttgattgtga    1080
ggcttctaat aaagtagtta ttagtagtgc cgcgcgcagc ggccagagac cgagccctaa    1140
ggagagtgcg gcgcttcccg aggcgtgcag ctgggaactg caactcatct gggttgtgcg    1200
cagaaggctg gggcaagcga gtagagaagt ggagcgtaag ccaggggcgt tgggggccgt    1260
gcgggtcggg cgcgtgccac gcccgcgggg tgaagtcgga gcgcggggcc tgctggagag    1320
aggagcgctg cggaccgagt aatggcaatg cagatgcagc ttgaagcaaa tgcagatact    1380
tcagtggaag aagaaagctt tggcccacaa cccatttcac ggttagagca gtgtggcata    1440
aatgccaacg atgtgaagaa attggaagaa gctggattcc atactgtgga ggctgttgcc    1500
tatgcgccaa agaaggagct aataaatatt aagggaatta gtgaagccaa agctgataaa    1560
attctggctg aggcagctaa attagttcca atgggtttca ccactgcaac tgaattccac    1620
caaaggcggt cagagatcat acagattact actggctcca aagagcttga caaactactt    1680
caaggtggaa ttgagactgg atctatcaca gaaatgtttg gagaattccg aactgggaag    1740
acccagatct gtcatacgct agctgtcacc tgccagcttc ccattgaccg ggtggaggt    1800 gaaggaaagg ccatgtacat tgacactgag ggtacctta ggccagaacg gctgctggca    1860
gtggctgaga ggtatggtct ctctggcagt gatgtcctgg ataatgtagc atatgctcga    1920
gcgttcaaca cagaccacca gacccagctc ctttatcaag catcagccat gatggtagaa    1980
tctaggtatg cactgcttat tgtagacagt gccaccgccc tttacagaac agactactcg    2040
ggtcgaggtg agctttcagc caggcagatg cacttggcca ggtttctgcg gatgcttctg    2100
cgactcgctg atgagtttgg tgtagcagtg gtaatcacta atcaggtggt agctcaagtg    2160
gatggagcag cgatgtttgc tgctgatccc aaaaaaccta ttggaggaaa tatcatcgcc    2220
catgcatca                                                            2229
```

<210> SEQ ID NO 2  
<211> LENGTH: 15  
<212> TYPE: DNA  
<213> ORGANISM: Artificial Sequence  
<220> FEATURE:  
<223> OTHER INFORMATION: Description of Artificial Sequence: Synthetic.

<400> SEQUENCE: 2

```
ggcttcacta attcc                                                       15
```

<210> SEQ ID NO 3  
<211> LENGTH: 15

```
<212> TYPE: DNA
<213> ORGANISM: Artificial Sequence
<220> FEATURE:
<223> OTHER INFORMATION: Description of Artificial Sequence: Synthetic.

<400> SEQUENCE: 3
cgtatgacag atctg                                                        15

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic.

<400> SEQUENCE: 4
gccacactgc tctaaccg                                                     18

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic.

<400> SEQUENCE: 5
ggtctctggc cgctgcgcgc gg                                                22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic.

<400> SEQUENCE: 6
gcgggcgtgg cacgcgcccg                                                   20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic.

<400> SEQUENCE: 7
cccaagtcat tcctaaggca cc                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic.

<400> SEQUENCE: 8
gggagtacag gcgcaagaca cc                                                22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic.

<400> SEQUENCE: 9
```

-continued

```
cgatccacct gcctcggcct ccc                                            23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic.

<400> SEQUENCE: 10
cctcaggcta tagagtagct ggg                                            23
```

ANTISENSE INHIBITION OF RAD51

This is a continuation-in-part of pending application Serial No. 60/119,578, filed Feb. 10, 1999.

FIELD OF THE INVENTION

The invention relates to methods of inhibiting the proliferation of cells and sensitizing cells to radiation therapy and DNA damaging chemotherapeutics, and in particular, treating cancer cells and individuals in vivo, including intra-operative treatments, by administration of Rad51 inhibitors including antisense molecules.

BACKGROUND OF THE INVENTION

The control of the proliferation of cells is of interest. For example, inhibition of the proliferation of cells is useful in treating a number of disorders such as cancer, autoimmune disease, arthritis, inflammatory bowel disease, proliferation induced after medical procedures, and many other instances. Therefore, a number of approaches have been taken which are meant to inhibit the proliferation of cells. For example, chemotherapeutics are intended to inhibit proliferation or kill cancerous cells. However, while there have been many approaches to treating disorders requiring the inhibition of cell proliferation, there is still a need to identify more efficient treatments, particularly treatments which are sensitive and which have limited side effects.

In one approach, radiation is a major treatment mode for both children and adults with high grade gliomas. Although low linear energy transfer irradiation has been shown to have some beneficial effects on the treatment of astrocytic tumors, most malignant gliomas are radioresistant so that various methods of improving the therapeutic ratio in their treatment have been explored. The efficacy of fractionated irradiation, which is commonly employed in clinical practice, depends on four facts: redistribution of tumor cells in the cell cycle, repopulation, reoxygenation, and repair of sublethal damage. These factors have generated several approaches which have been applied in clinical practice. These include accelerated fractionation so as to reduce tumor repopulation, radiosensitization of hypoxic cells by hyperbaric oxygen and nitroimidazoles, and combination with chemotherapeutic agents such as BCNU and vincristine [9–11]. So far, however, none of these procedures has resulted in satisfactory outcome for the treatment of malignant gliomas.

One study has reported that Rad51 antisense inhibition enhances radiosensitivity in normal cells, in vitro. Taki, et al., Biochemical and Biophysical Res. Comm., 223:434–438 (1996). However, this study does not report on the affects of Rad51 antisense inhibition in abnormal cells, such as tumor cells, nor does this study report on the affects of Rad51 antisense inhibition in vivo.

Rad51 is of interest because it is detected in every proliferating cell. It is believed that Rad51is within the family of proteins involved in repairing DNA damage, such as double-strand breaks in DNA caused by ionizing radiation and some alkylating agents, which lead to cell death if not repaired. Several genes related to double-strand break repair have been isolated from *E. coli* and *S. cerevisia* (Roca and Cox (1990); Shinohara (1992)). In most prokaryotes, including *E. coli* RecA protein or RecA-like protein plays an essential role in homologous recombination and in a variety of SOS responses to DNA damage (Kowalczykowski (1987)). In yeasts, which are lower eukaryotes, genes of the RAD52 epistasis group (RAD50-RAD57) have been identified by mutants not only as being deficient in their capability of DNA damage repair caused by ionizing radiation but also as having impaired capacity for mitotic and meiotic recombination (Resnick (1987); Friedberg (1988)). The Rad51 gene has been cloned and its product shown to be structurally similar to *E. coli* RecA protein with ATP-dependent DNA binding activity (Aboussekhara (1992); Basile (1992)). One study shows a mouse homologue of the yeast Rad51 gene that functionally complements a Rad51 mutation of *S. cerevisiae* with sensitivity to methylmethanesulfonate, a double-strand breaking agent (Morita (1993)).

The present invention, for the first time, provides methods to inhibit cell proliferation comprising administration of a Rad51 inhibitor. The invention further provides Rad51 inhibitor molecules that disrupt mammalian double stranded break repair. Moreover, the invention provides methods to treat diseased cells or individuals by administering a composition comprising a Rad51 inhibitor. Furthermore, the invention provides methods of inhibiting Rad51 expression in vivo using Rad51 inhibitors. Additionally, the invention provides methods of inducing sensitization to radiation, aklylating agents and other DNA damaging chemotherapeutics in vivo using Rad51 inhibitors. Also, the invention provides Rad51 inhibitors that are antisense molecules. Other aspects of the invention are described below.

SUMMARY OF THE INVENTION

The present invention provides methods for inhibiting cell proliferation in an individual comprising administering to the individual a composition comprising a Rad51 inhibitor. Also provided herein is a method for inhibiting the growth of a cell comprising administering to said cell a composition comprising a Rad51 inhibitor. Such methods can further include the step of providing radiation or alkylating agents after administration of said Rad51 inhibitor. In preferred embodiments the methods are performed in vivo and/or on cancerous cells and can be used with intra-operative treatments.

In a another aspect, the present invention provides methods for inhibiting cell proliferation in an individual in vivo comprising administering to the individual a composition comprising a Rad51 antisense molecule. Also provided herein is a method for inhibiting the growth of a cancerous cell comprising administering to said cell a composition comprising a Rad51 antisense molecule.

In another aspect, provided herein is a method for inducing sensitivity to radiation and DNA damaging chemotherapeutics in an individual in vivo comprising administering to said individual a composition comprising a Rad51 antisense molecule. Also provided herein is method for inducing sensitivity to radiation and alkylating chemotherapeutics in a cancerous cell comprising administering to said cell a composition comprising a Rad51 antisense molecule. In one embodiment, the methods provided herein also include the step of administering radiation or alkylating chemotherapeutic agents to a cell.

In one aspect, the method of sensitizing a cell to radiation or DNA damaging agents comprises administering to a cell at least one antisense molecule having a sequence selected from the group consisting of AS4, AS5, AS6, AS7, AS8 and AS9. Also provided herein is a method of prolonging survival in an individual with cancer comprising administering to said individual at least one antisense molecule having a sequence selected from the group consisting of AS4, AS5, AS6, AS7, AS8 and AS9.

In a further aspect of the invention, administration of the compositions herein comprises localized delivery of said Rad51 antisense molecule. Moreover, said methods provided herein may further comprise radiation treatment and/or chemotherapeutic treatment of said patient.

Further provided herein are kits for diagnosing and/or treating cancer comprising a Rad51 antisense molecule. In one aspect, the kit is for adjunctive therapy for cancer. In a preferred embodiment, the kit comprises at least one of packaging, instructions, suitable buffers, controls, and pharmaceutically acceptable carriers.

BRIEF DESCRIPTION OF THE DRAWINGS

FIG. 3B shows the specific inhibition of Rad51 by antisense oligonucleotides. Rad51 was monitored by Western blotting. c-Raf was used as an internal loading control. Rad51 expression is inhibited more than 90% by using either single antisense oligonucleotides or combinations of antisense oligonucleotides at a concentration of 200 nM (FIG. 3A).

FIGS. 9A and 9B show the human Rad51 mRNA sequence (SEQ ID NO:1) wherein the regions complementary to antisense molecules are underlined.

DETAILED DESCRIPTION OF THE INVENTION

Figure 1:
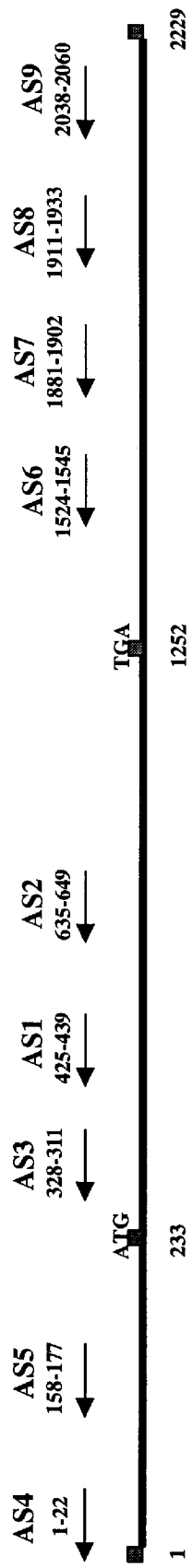
FIG. 1 depicts a map of Rad51 antisense oligonucleotides. Rad51 antisense oligonucleotides, AS1 to AS3, map to the coding region of Rad51 and are homologous to both human and mouse sequences. AS4 and AS5 map to the 5' untranslated region and AS6 to AS9 map to the 3' untranslated region.

The present invention is based on the series of discoveries relating to the pivotal role that Rad51 plays in a number of cellular functions, including those involved in disease states. In particular, the present invention is based in part on inhibiting Rad51.

A Rad51 inhibitor as defined herein inhibits expression or translation of a Rad51 nucleic acid or the biological activity of a Rad51 peptide by at least 30%, more preferably 40%, more preferably 50%, more preferably 70%, more preferably 90%, and most preferably by at least 95%. In one embodiment herein, a Rad51 inhibitor inhibits expression or translation of a Rad51 nucleic acid or the expression or activity of a Rad51 protein by 100%.

By "biological activity" of Rad51 herein is meant one of the biological activities of Rad51, including, but not limited to, the known Rad51 DNA dependent ATPase activity, the nucleic acid strand exchange activity, the formation of foci, single-stranded and double-stranded binding activities, filament formation (similar to the recA filament of yeast), pairing activity (D-loop formation), etc. As shown herein, in one aspect, by inhibiting the biological activity of Rad51, cell proliferation is inhibited. In another aspect, a Rad51 inhibitor is defined as a molecule that disrupts mammalian double stranded break repair. In a further aspect, a Rad51 inhibitor results in the cells containing it to be more sensitive to radiation and/or chemotherapeutic agents.

In one embodiment herein, inhibitors of Rad51 include those identified by the methods such as those which identify changes in Rad51 biological activity, expression or translation, as well as downregulators or inhibitors of Rad51 as defined above. In another aspect, Rad51 inhibitors can include known inhibitors of RecA and/or known inhibitors that sensitize cells to radiation and also affect aspects of recombination in vivo. Inhibitors of interest also include but are not limited to peptide inhibitors of Rad51 (including but not limited to amino acids 94–160 and 264–315 of p53 and Rad51 antibodies (further described below) including but not limited to single chain antibodies), small molecules, nucleotide analogues (including but not limited to ADP analogues, ATPγS), minor groove DNA binding drugs as inhibitors of Rad51 (including but not limited to distamycin and derivatives thereof), known radiation sensitizers (e.g., xanthine and xanthine derivatives including caffeine) on the biochemical activities of Rad51, antigenes against Rad51, particularly those which inhibit transcription by locked hybrids, and antisense molecules. The inhibitor can inhibit Rad51 directly or indirectly, preferably directly by interacting with at least a portion of the Rad51 nucleic acid or protein. Additionally, the inhibitors herein can be utilized individually or in combination with each other.

Generally, the Rad51 antisense molecule is at least about 10 nucleotides in length, more preferably at least 12, and most preferably at least 15 nucleotides in length. The skilled artisan understands that the length can extend from 10 nucleotides or more to any length which still allows binding to the Rad51 nucleic acid. In a preferred embodiment herein, the length is about 30 nucleotides, more preferably about 25 nucleotides, and most preferably about 12 to 25 nucleotides in length.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The nucleic acids herein, including antisense nucleic acids, and further described above, are recombinant nucleic acids. A recombinant nucleic acid is distinguished from naturally occurring nucleic acid by at least one or more characteristics. For example, the nucleic acid may be isolated or purified away from some or all of the nucleic acids and compounds with which it is normally associated in its wild type host, and thus may be substantially pure. For example, an isolated nucleic acid is unaccompanied by at least some of the material with which it is normally associated in its natural state, preferably constituting at least about 0.5%, more preferably at least about 5% by weight of the total nucleic acid in a given sample. A substantially pure nucleic acid comprises at least about 75% by weight of the total nucleic acid, with at least about 80% being preferred, and at least about 90% being particularly preferred. Alternatively, the recombinant molecule could be made synthetically, i.e., by a polymerase chain reaction, and does not need to have been expressed to be formed. The definition includes the production of a nucleic acid from one organism in a different organism or host cell.

The antisense molecules hybridize under normal intracellular conditions to the target nucleic acid to inhibit Rad51 expression or translation. The target nucleic acid is either DNA or RNA. In one embodiment, the antisense molecules bind to regulatory sequences for Rad51. In one embodiment, the antisense molecules bind to 5' or 3' untranslated regions directly adjacent to the coding region. Preferably, the antisense molecules bind to the nucleic acid within 1000 nucleotides of the coding region, either upstream from the start or downstream from the stop codon. In a preferred embodiment, the antisense molecules bind within the coding region of the Rad51 molecule. More preferably, the antisense molecule is selected from the group consisting of AS4, AS5, AS6, AS7, AS8 and AS9 as indicated in FIG. 1 and Table 1 below. Table 1 includes the recitation of "R51" before the same corresponding antisense, but for example, "AS4" and "R51AS4" are used interchangeably herein. In one embodiment, the antisense molecules are not directed to the structural gene; this embodiment is particularly preferred when the antisense molecule is not combined with another antisense molecule. It is understood that any of the antisense molecules can be combined.

In one embodiment combinations of antisense molecules are utilized. In one embodiment, at least antisense molecule is selected from the 3' untranslated region.

The term "antibody" is used in the broadest sense and specifically covers single anti-Rad51 monoclonal antibodies (including agonist, antagonist, and neutralizing antibodies) and anti-Rad51 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

The anti-Rad51 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Rad51 polypeptide or a fusion protein thereof. It may be useful to conjugate the immunizing agent to a protein known to be immunogenic in the mammal being immunized.

Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-Rad51 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the Rad51 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against Rad51. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-Rad51 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

Bispecific antibodies are monoclonal, preferably human or humanized, antibodies that have binding specificities for at least two different antigens. In the present case, one of the binding specificities is for the Rad51, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random-assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In one embodiment, Rad51 includes homologues of Rad51. In one aspect, Rad51 homologues can be defined by the Rad51 role in recombinational repair. In another aspect, Rad51 genes encode proteins which share significant sequence identity with residues 33–240 of *E. coli* RecA protein, which has been identified as a homologous core region in the literature. Rad51 homologues include RecA and Rad51 homologues in yeast and in mammals. RecA and yeast Rad51 have been cloned and are known in the art. Radding, Genetic Recom. 193–230 (1988); Radding, J. Biol. Chem. 266:5355–5358 (1991); Kowalczykoswski, et al., Annu. Rev. Biochem., 63:991–1043 (1994); Basile, et al., Mol. Cell. Biol., 12:3235–3246 (1992); Aboussekhara, et al., Mol. Cell. Biol., 12:3224–3234 (1992). Genes homologous to *E. Coli* recA and yeast Rad51 have been isolated from all groups of eukaryotes, including mammals. Morita, et al., PNAS USA, 90:6577–6580 (1993); Shinohara, et al., Nature Genet., 4:239–243 (1993); Heyer, Experentia, 50:223–233 (1994); Maeshima, et al., Gene, 160:195–200 (1995). Rad51 has been identified in humans, mice, chicken, *S. Cerevisiae, S. Pombe* and Mci3 of *Neurospora crassa*. Human Rad51 homologues include Rad51, Rad51 B, Rad51C, Rad51D, XRCC2 and XRCC3. Albala, et al., Genomics, 46:476–479 (1997); Dosanjh, et al., Nucleic Acids Res, 26:1179(1998); Pittman, et al., Genomics, 49:103–11 (1998); Cartwright, et al., Nucleic acids Res, 26:3084–3089 (1998); Liu, et al., Mol Cell, 1:783–793 (1998).

In an embodiment provided herein, the invention provides methods of treating disease states requiring inhibition of cellular proliferation. In a preferred embodiment, the disease state requires inhibition of at least one of Rad51 expression, translation or the biological activity of Rad51 as described herein. As will be appreciated by those in the art, a disease state means either that an individual has the disease, or is at risk to develop the disease.

Disease states which can be treated by the methods and compositions provided herein include, but are not limited to hyperproliferative disorders. More particular, the methods can be used to treat, but are not limited to treating, cancer (further discussed below), autoimmune disease, arthritis, graft rejection, inflammatory bowel disease, proliferation induced after medical procedures, including, but not limited to, surgery, angioplasty, and the like. Thus, in one embodiment, the invention herein includes application to cells or individuals afflicted or impending affliction with any one of these disorders.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-L-eydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

The individual, or patient, is generally a human subject, although as will be appreciated by those in the art, the patient may be animal as well. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient. In a preferred embodiment, the individual requires inhibition of cell proliferation. More preferably, the individual has cancer or a hyperproliferative cell condition.

The compositions provided herein may be administered in a physiologically acceptable carrier to a host, as previously described. Preferred methods of administration include systemic or direct administration to a tumor cavity or cerebrospinal fluid (CSF).

In a preferred embodiment, these compositions can be administered to a cell or patient, as is outlined above and generally known in the art for gene therapy applications. In gene therapy applications, the antisense molecules are introduced into cells in order to achieve inhibition of Rad51. "Gene therapy" includes both conventional gene therapy where a lasting effect is achieved by a single treatment, and the administration of gene therapeutic agents, which involves the one time or repeated administration of a therapeutically effective DNA or RNA. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146[1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]).

In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

In one aspect herein, the methods are used to knock out Rad51 in animal models or in cells to form models for further research. The knock out animals can then be used as control animals or for screening for regulators of Rad51 activity.

The antisense molecules can be combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

In one aspect, the Rad51 inhibitors herein induce sensitivity to alkylating agents and radiation. Induced sensitivity (also called sensitization or hypersensitivity) can be measured by the cells tolerance to radiation or alkylating agents. For example, sensitivity, which can be measured, i.e., by toxicity, occurs if it is increased by at least 20%, more preferably at least 40%, more preferably at least 60%, more preferably at least 80%, and most preferably by 100% to 200% or more.

In an embodiment herein, the methods comprising administering the Rad51 inhibitors provided herein further comprise administering an alkylating agent or radiation. For the purposes of the present application the term ionizing radiation shall mean all forms of radiation, including but not limited to alpha, beta and gamma radiation and ultra violet light, which are capable of directly or indirectly damaging the genetic material of a cell or virus. The term irradiation shall mean the exposure of a sample of interest to ionizing radiation, and term radiosensitive shall refer to cells or individuals which display unusual adverse consequences after receiving moderate, or medically acceptable (i.e., non-lethal diagnostic or therapeutic doses), exposure to ionizing irradiation. Alkylating agents include BCNU, CCNU and MMS. Other preferred agents include crosslinking agents such as cisplatin and carboplabim.

In one embodiment herein, the Rad51 inhibitors provided herein are administered to prolong the survival time of an individual suffering from a disease state requiring the inhibition of the proliferation of cells. In a preferred embodiment, the individual is further administered radiation or an alkylating agent.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are specifically incorporated by reference in their entirety.

EXAMPLES

Example 1

Down-regulation of Human Rad51 Protein by Antisense Oligodeoxynucleotides in Human Breast, Brain and Prostate Cells An essentially complete reduction in the expression of Rad51 protein by using specific human Rad51 antisense oligodeoxynucleotides in a variety of human tumor cell lines has been achieved herein. The human Rad51 mRNA sequence is shown in FIG. 9A and 9B wherein the regions complementary to the antisense molecules are underlined.

Materials and Methods

Methods of cloning and expression of HsRad51 gene in *E. coli*, purification of recombinant HsRad51 protein with six histidine residues at its amino terminal end and preparation of polyclonal antibodies against HsRad51 protein were prepared using standard methods known in the art.

Detection of Rad51 Protein by Western Blotting with anti-Rad51 Antibodies.

For determination of protein levels by Western blot, cellular extracts were prepared as follows. Cells were harvested by scraping; washed with PBS and pelleted by centrifugation. Cell pellets (from 100 mm plate) were resuspended with 200 $\mu$l B3 buffer containing protease inhibitors shaken at 4° C. for 10 min and centrifuge at 12,000 rpm at 4° C. in Tomy microcentrifuge for 10 minutes. To make 1 liter of B3 buffer, add 1 ml of NP-40, 50 ml of 5 M NaCl, 10 ml of 0.5 ml EDTA, 50 ml of 1 M TrisHCl at pH7.5 to 889 ml $dH_2O$. The day of cell harvest protease inhibitors were added to B3 buffer (aprotinin, leupeptin and pepstatin to a final concentration of 2 $\mu$g/ml, 5 $\mu$g/ml and 0.7 $\mu$g/ml, respectively). Supernatants were saved for Western blot analysis. Sample protein concentrations were determined by the Bradford Assay (BioRad; Richmond, Calif.). Typically, 50 $\mu$g of protein were separated by electrophoresis at 120 V, 150 mAmp for 1.5 hours on a 10% SDS-polyacrylamide mini-gel (Mini Protean II, BioRad; Richmond, Calif.). Protein was transferred to nitrocellulose (Protran nitrocellulose, Schleicher and Schuell; Keene, N.H.) by transfer for 15 min at 15V, 40 mAmp using a Trans-Blot SD Semi-dry Transfer Cell (BioRad; Richmond, Calif.). Blocking of nitrocellulose filters was conducted overnight at 4° C. in 5% milk in PBS/0.2% Triton X-100. The minimum blocking time is 10 minutes. The liquid was discarded and 5 ml of Rad51 polyclonal antibody was added (Ab1 from Oncogene Research Products, Calbiochem; Cambridge, Mass.; diluted 1:500). As a centrifuge, we used Raf antibody (c-Raf-1 from Transduction Laboratories; Lexington, Ky.; diluted 1:100). Nitrocellulose membranes were shaken at RT for 1 hour, washed 3 times for 5 minutes in Tris buffered saline (TBS) containing 0.2% Triton X-100, and blocked again for 10 minutes with 5% milk in TBS containing 0.2% Triton X-100. Secondary antibody (goat anti-rabbit at 1:1000 for Rad51 and anti-mouse at 1:2000 for Raf antibody) was added in fresh TBS containing 0.2% Tritan x-100 and milk and shaken for 20–40 minutes, washed 3 times 10 minutes with TBS containing 0.2% Triton X-100. Western blots were developed using Super Signal (Pierce; Rockford, Ill.) according to kit protocol. Expose to Kodak X-OMAT AR film for 10 sec to 1 min.

Downregulation of Rad51 by Antisense Oligonucleotides.

Cells were plated at $1 \times 10^6$ cells in 100 mm tissue culture plates (to achieve approximately 50% confluency the following day), and incubated overnight at 37° C. and 5% $CO_2$. The next day cells were transfected with antisense, sense or no oligonucleotide. The transfection mixture was set up as follows: 4 µl of Cytofectin GSV reagent (Glen Research; Sterling, Va.) at 2 µg/ml final concentration; 8 µl of oligonucleotide in 10 mM TrisHcl pH 7.5, 0.1 mM EDTA at 20–200 nM final concentration; mix with 788 µl Opti-MEM and incubate for 15 minutes at room temperature. Add 3.2 mls of Opti-MEM medium (Life Technologies, Inc) and mix well for a total transfection volume of 4 mls. Culture plates were washed with approximately 1 mL of Opti-Mem medium, 4 mls of transfection mixture was added to 100 mm tissue culture plates, and incubated for 4 hours at 37° C. and 5% $CO_2$. The transfection mix was replaced with normal media containing the same final concentration of oligo (no lipid) and incubated overnight at 37° C. The transfection procedure was repeated at 24 hours. The cells were harvested at 48 hours and analyzed protein levels were by Western blotting.

Combination of Rad51Antisense and Cisplatin Treatment of Tumor Cells.

Cells were treated with antisense, sense or no oligonucleotide as described above with the following modification. On day two after the second transfection, cells were treated with various concentrations (0, 20, 50, 100, µM) of cisplatin for 1 hour, and then washed and cultured overnight in normal growth medium containing 10% FCS at 37° C., 5% $CO_2$. Viable cell number was determined at the appropriate times (24, 48, 72 hours) following oligonucleotide treatment by direct counting using a hemacytometer. Each experimental condition was performed in triplicate. Cell viability was determined by trypan blue staining.

Results

Rad51 Expression in Primary Human Breast Epithelial Cells Compared to Human Breast Tumor Cells.

Figure 2:
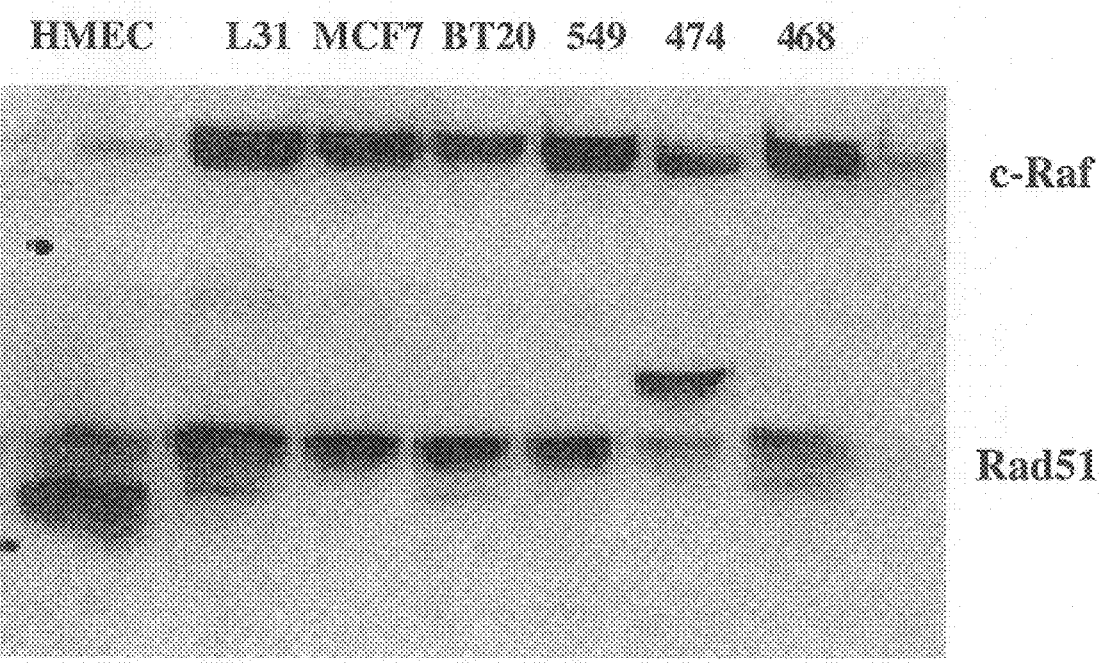
FIG. 2 shows the comparison of Rad51 in primary breast epithelial cells versus breast tumor cell lines wherein Western blots from extracts of human mammary epithelial cells (HMEC) and breast tumor cell lines (L31, MCF7, BT20, BT549, BT474, BT468) are shown. Rad51A and control c-Raf proteins are detected by polyclonal antibody probes as indicated on the right. Two bands are only detected with Rad51A antibodies in HMEC extracts.
Figure 3:
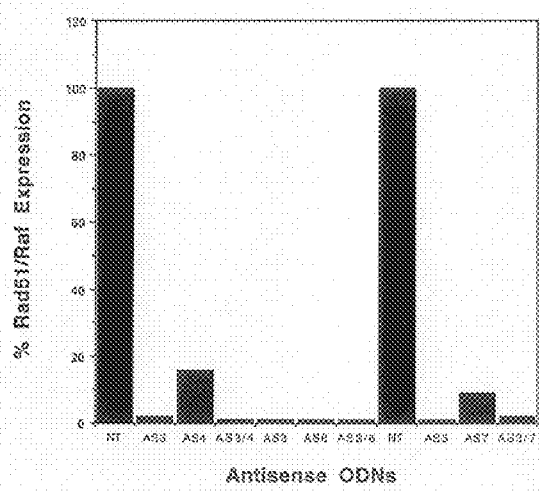
FIGS. 3A and 3B show Rad51 inhibition in MDA-MB-231 human breast tumor cells by Rad51 antisense.
Figure 3:
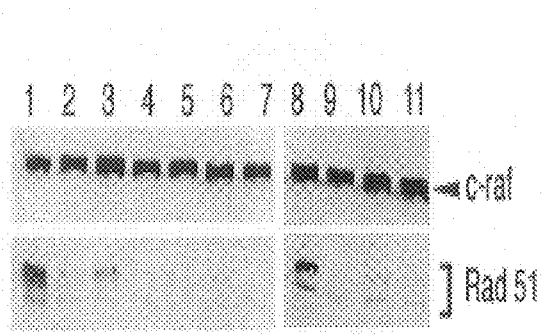
Figure 4:
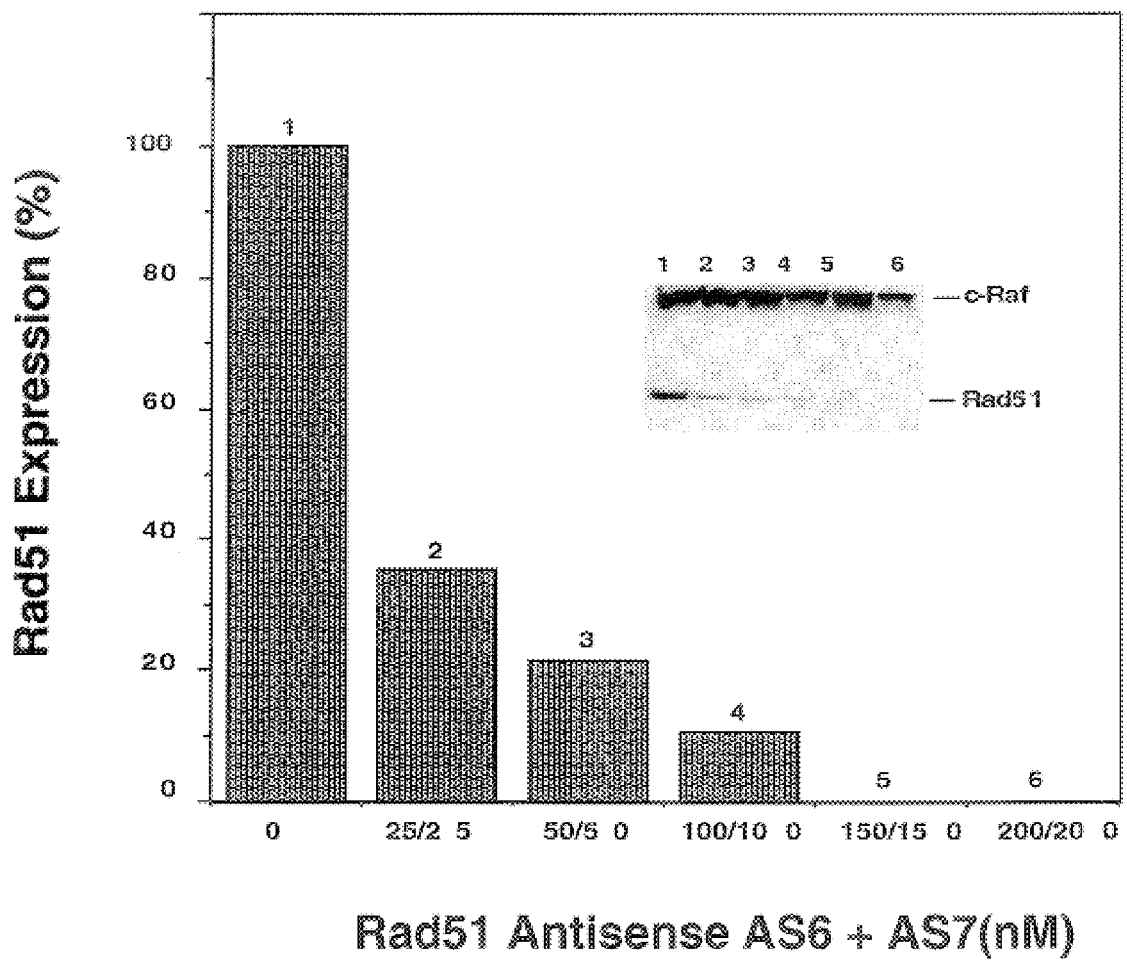
FIG. 4 shows titration of Rad51 antisense in MDA-MB-231 breast tumor cells. Different concentrations of AS6/AS7 antisense oligonucleotides were used to determine the lowest amount of antisense to inhibit Rad51 without having cytotoxic effects. As low as 25 nM each of AS6/AS7 oligonucleotide was enough to inhibit Rad51 expression by more than 50%. Antisense oligonucleotides at concentrations more than 100 nM inhibited Rad51 expression almost entirely.
Figure 5:
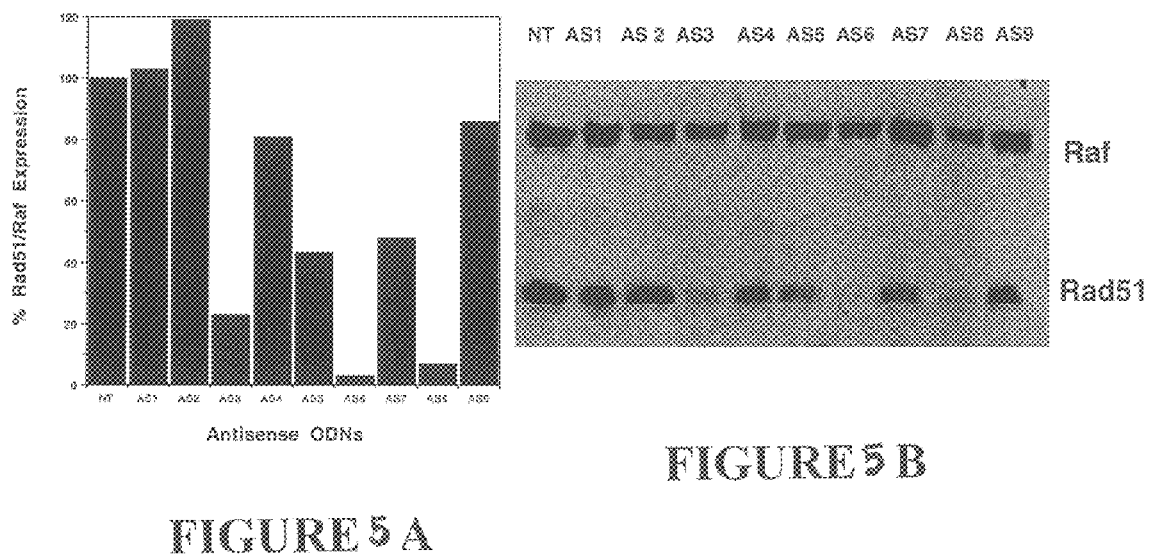
FIG. 5 shows Rad51 inhibition in U251 human brain tumor cells by Rad51 antisense. Antisense oligonucleotides AS1 through AS9 were used at a concentration of 200 nM to inhibit Rad51 expression in brain tumor cells. Rad51 protein was monitored by Western blotting and c-Raf was used as an internal loading control. More than 80% inhibition of Rad51 was achieved using AS6, AS8 and AS3.
Figure 6:
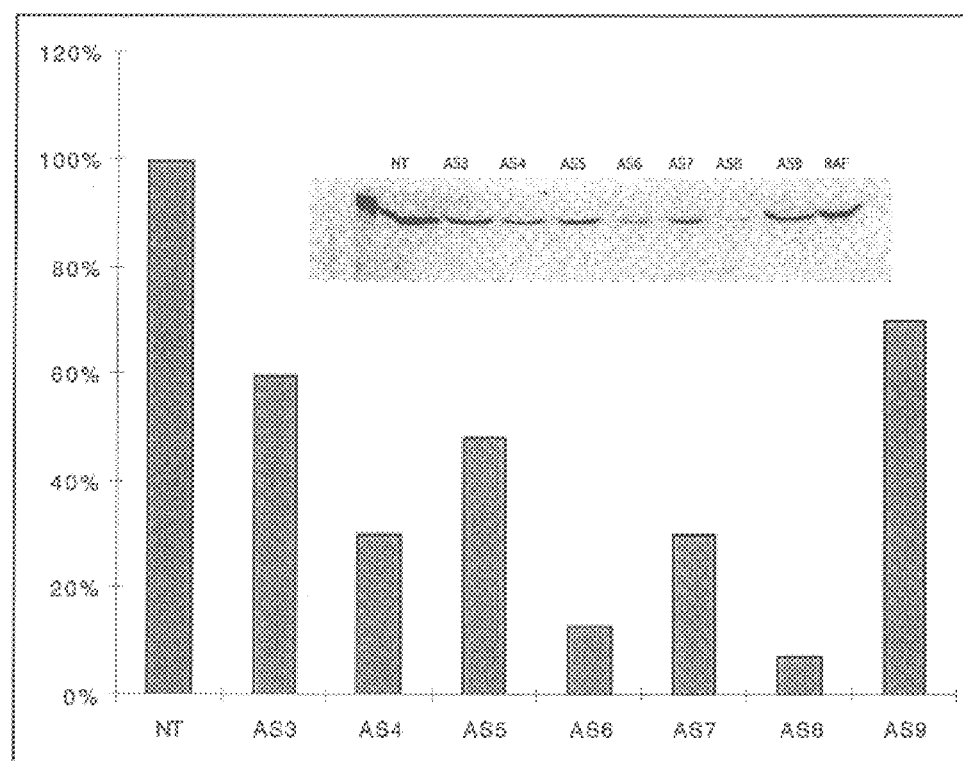
FIG. 6 shows Rad51 inhibition in LNCaP human prostate tumor cells by Rad51 antisense. Antisense oligonucleotides AS1 through AS9 were used at a concentration of 200 nM to inhibit Rad51 expression in prostate tumor cells. Rad51 protein was monitored by Western blotting and c-Raf was used as an internal loading control. More than 80% inhibition of Rad51 was achieved using AS6 and AS8 while the other antisense oligonucleotides inhibited Rad51 to various extents.

Rad51 protein expression was compared in several different breast tumor cell lines and primary breast epithelial cells served as controls. Rad51 protein was monitored by Western blotting using Rad51 and c-Raf specific antibodies. C-Raf was used as an internal loading control. Two Rad51 bands were detected in primary breast epithelial breast cells, one band corresponded to the full length Rad51 and the other was a lower molecular weight product (FIG. 2, lane 1). It is probable that the lower molecular weight band is a product of Rad51 protein degradation. All the breast tumor cell lines showed predominantly one band that corresponded to the full length Rad51 protein (FIG. 2, lanes 2 to 7). In one breast tumor cell line (BT549), Rad51 migrated slower than the rest of the samples. It is possible that this Rad51 is modified (phosphorylated or glycosylated) in this particular cell line.

Specific and Efficient Downregulation of Human Rad51 Protein by Rad51 Antisense Oligo-Deoxynucleotides in Human Breast, Brain and Prostate Cells.

We designed nine potentially specific antisense ODNs targeted against the 5' untranslated region (AS4, AS5), the 3' untranslated region (AS6–AS9) and the coding region (AS1 to AS3 of Rad51 mRNA). Sequences of all the sense, scrambled and antisense ODNs, used in the study are shown in Table 1 and the position of each of the antisense ODN in the Rad51 sequence is shown in FIG. 1. These antisense ODNs were tested against human cell lines derived from human breast, brain and prostate tumors. A nearly complete reduction in the expression of Rad51 protein was observed using these specific human Rad51 antisense oligodeoxynucleotides (ODNs) in a variety of human tumor cell lines (FIGS. 3 to 6). Combinations of antisense oligonucleotides were additive in downregulating Rad51. In addition, antisense oligonucleotides targeted against the untranslated regions were significantly more effective than the antisense ODNs that targeted the coding regions of Rad51 gene.

TABLE 1

Antisense Oligonucleotide Sequences used in this study

ANTISENSE IN CODING REGION

1. R51AS1- 5'- (P=S) GGC TTC ACT AAT TCC-3' (SEQ ID NO:2)
2. R51AS2- 5'- (P=S) CGT ATG ACA GAT CTG-3' (SEQ ID NO:3)
3. R51AS3- 5' (P=S) GCC ACA CTG CTC TAA CCG 3' (SEQ ID NO:4)

ANTISENSE IN 5' UNTRANSLATED REGION

4. R51AS4- 5' (P=S) GGT CTC TGG CCG CTG CGC GCG G-3' (SEQ ID NO:5)
5. R51AS5- 5' (P=S) GCG GGC GTG GCA CGC GCC CG-3' (SEQ ID NO:6)

ANTISENSE IN 3' UNTRANSLATED REGION

6. R51AS6- 5' (P=S) CCC AAG TCA TTC CTA AGG CAC C-3' (SEQ ID NO:7)
7. RS1AS7- 5' (P=S) GGG AGT ACA GGC GCA AGA CAC C-3' (SEQ ID NO:8)
8. R51AS8- 5' (P=S) CGA TCC ACC TGC CTC GGC CTC CC-3' (SEQ ID NO:9)
9. R51AS9- 5' (P=S) CCT CAG GCT ATA GAG TAG CTG GG-3' (SEQ ID NO:10)

Effect of Antisense ODNs on Cell Proliferation.

Figure 7:
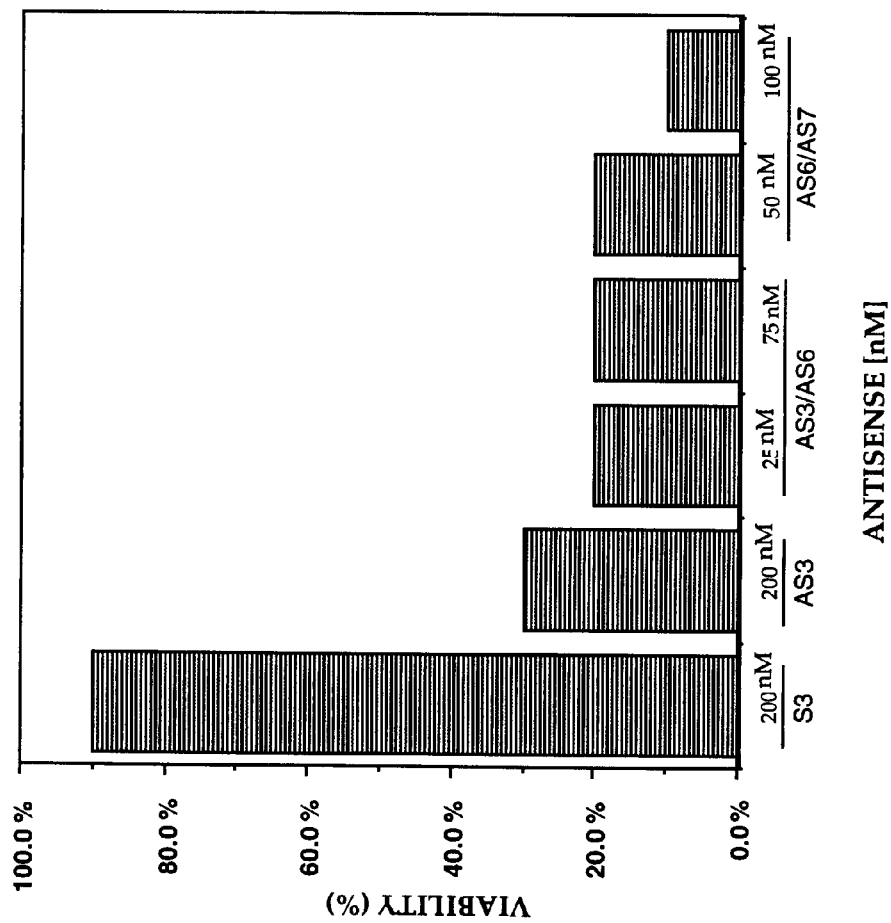
FIG. 7 shows the effect of Rad51A antisense ODNs on cell proliferation. Rad51A antisense oligonucleotides were used at concentrations ranging from 25 nM to 200 nM in MDA-MB-231 breast tumor cells and cell growth and viability was monitored. Control sense oligonucleotides were used as the control. Rad51A antisense ODNs treatment alone or in combinations (AS6/AS7) inhibited proliferation by 80%. Shown is the viability of cells 48 hours after treatment with Rad51A antisense ODNs.

Treatment of MDM-MB-231 breast tumor cells with antisense ODNs significantly inhibited the cell growth (FIG. 7). Incubation with sense or scrambled ODNs had little or no effect on cell growth. Treatment of cells with antisense ODNs AS3 or a combination of AS3/AS6 or AS6/AS7 at a concentration of 100 nM resulted in more than 80% inhibition of cell growth. This result is consistent with published dated that Rad51 is an essential in DNA metabolism and Rad51 knockout or inhibition results in lethal phenotype.

Rad51 Downregulation Sensitizes Breast Tumor Cells to Cisplatin.

Figure 8:
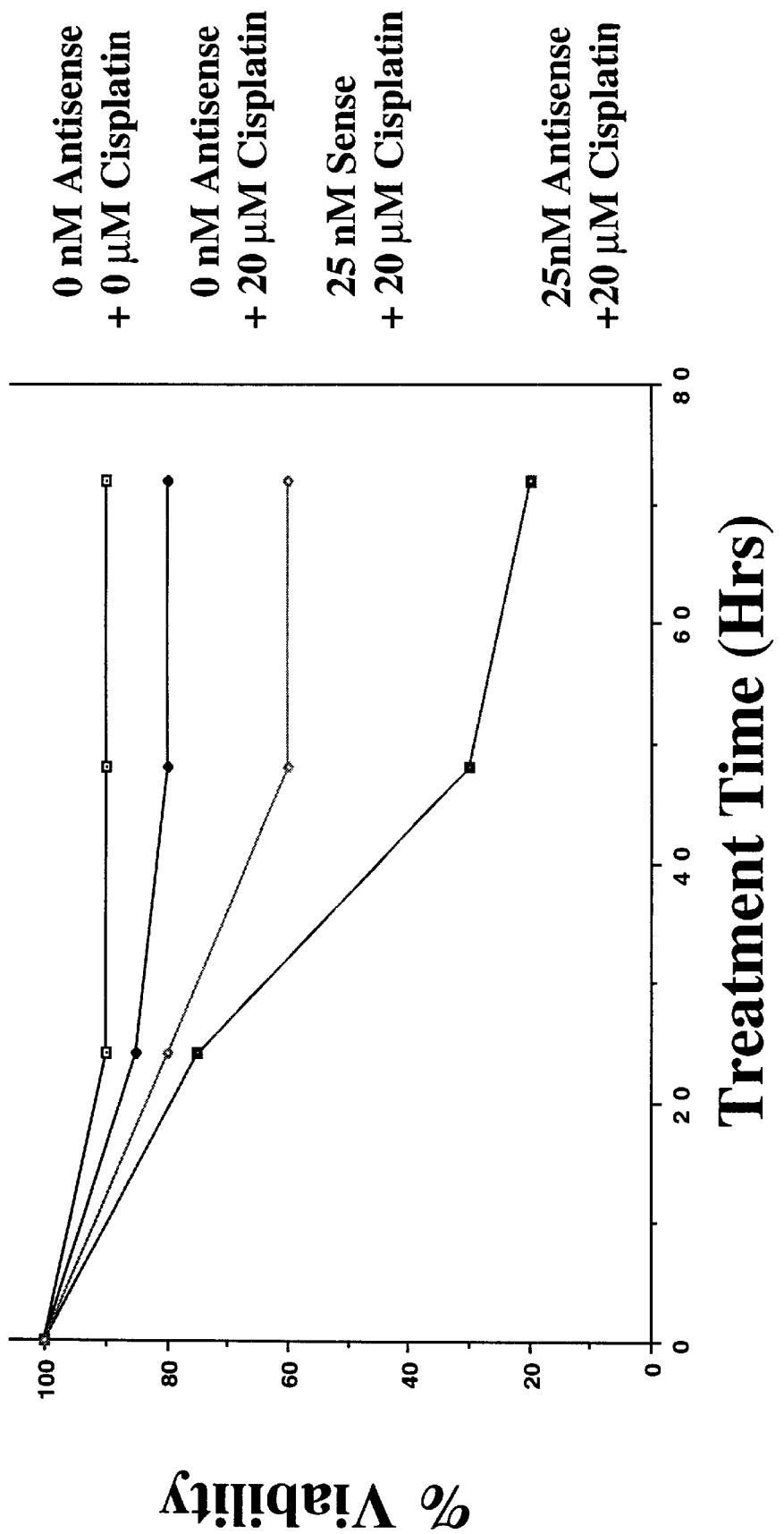
FIG. 8 shows Rad51 inhibition senstizes tumor cells to treatment with cisplatin. Rad51 antisense oligonucleotides (AS6) were used at a concentration of 25 nM to inhibit Rad51 expression in MDA-MB-231 breast tumor cells and the cells were treated with 20 $\mu$M of cisplatin for various periods of time. Cells treated with Rad51 antisense were more sensitive to cisplatin compared to the controls treated either with Rad51 sense oligonucleotides and cisplatin or cells treated with cisplatin alone. Cells without any treatment with either antisense or cisplatin were also used as controls.

We used a concentration of antisense ODN that downregulated Rad51 but cell growth. Similarly, we used cisplatin at a non-cytotoxic concentration (20 uM). MDA-MB-231 cells treated with both cisplatin and Rad51 antisense inhibitors were killed more efficiently than the cells treated with either cisplatin or antisense ODN alone (FIG. 8). This result shows that Rad51 downregulation sensitizes cells to cisplatin treatment.

Rad51 protein is a highly conserved eukaryotic homolog of prokaryotic RecA protein, which is important for recombination and repair of double-strand breaks in DNA. Without being bound by theory, increased amounts of Rad51 foci in tumor cells can occur because of any one of the three following reasons: 1) presence of mutations in Rad51, 2) increased stability of Rad51 due to increased half life, or 3) reorganization of Rad51. We show that there are differences in the way Rad51 protein appears to be stabilized or processed in primary cells compared to tumor cells. Comparison of Rad51 protein in primary breast cells versus breast tumor cells revealed that there are two bands of Rad51. One band corresponding to the full length Rad51 and another band of lower molecular weight possibly degraded form of Rad51 in primary breast cells whereas a single band of Rad51 is observed in a number of breast tumor cell lines tested. The two different bands of Rad51 are possible products of degradation of full length Rad51 protein. In primary cells, Rad51 may have a shorter half life and could be degraded faster into lower molecular weight products which would most probably be the inactive forms. Thus, Rad51 protein appears to be more stable and probably more active in tumor cells compared to normal cells. The aberrant expression of Rad51 in tumor cells is consistent with the observations of enhanced recombination and genomic instabilities, and radiation of DNA damaging chemical resistance in tumor cells.

Further without being bound by theory, it is possible that Rad51 overexpression could confer other advantages to tumor cells either by repairing DNA damage. Rad51 protein binds to both single-stranded and double-stranded DNA to form nucleoprotein filaments. DNA inside these filaments is known to be protected from nucleases. Rad51 expression is known to be high in rapidly dividing cells and in tumor cells. These observations have important diagnostic and therapeutic applications.

References

1. Roca, A. T., and Cox, M. M. (1990) *Crit. Rev. Biochem. Mol. Biol.* 25:415–456/
2. Shinohara, A., Ogawa, H., and Ogawa, T. (1992) *Cell* 69:457–470.
3. Kowalczykowski, S. C. (1991) *Annu. Rev. Biophys. Biophys. Chem.* 20:539–575.
4. Resnick, M. A. (1987) in Meiosis (Moens. P. B., Ed.), pp 157–210. Academic Press, New York.
5. Friedberg, E. C. (1988) *Microbiol. Rev.* 52:70–102.
6. Aboussekhara, A., Chanet, R., Adjiri, A., and Fabre, F. (1992) *Mol. Cell. Biol.* 12:3224–3234/
7. Basile, G., Aker, M., and Mortimer, R. K. (1992) *Mol. Cell. Biol.* 12:3235–3246.
8. Morita, T., Yoshimura, Y., Yamamoto, A., Murata, K., Mori, M., Yamamoto, H., and Matsushiro, A. (1993) *Proc. Natl. Acad. Sci. USA* 90:6577–6580.
9. Thames, H. D., Peters, L. J., and Winthers, H. R. (1983) *Int. J. Radiat. Oncol. Biol. Phys.* 9:127–138.
10. Reddy, E. K., Kimler, B. F., Henderson, S. D., and Morantz, R. A. (1980) in Radiation Sensitizers: Their Use in the Clinical Management of Cancer (Brady, L. W., Ed.), pp 457–471, Masson, N.Y.
11. Wheeler, K. T., and Kaufman, K. (1981) *Int. J. Radiat. Oncol. Biol. Phys.* 7:1065–1066.
12. Taki, T., Ohnishi, T., Yamamoto, A., Hiraga, S., Arita, N., Izumoto, S., Hayakawa, T., and Morita, T. (1996) *Biochem. Biophys. Res. Commun.* 223:434–438.
13. Muller, P. J., Shin, K. H., and Shin, D. H. (1983) *Can. J. Neurol. Sci.* 10:105–109.

We claim:

1. A Rad51 antisense molecule having a sequence targeted to the 5' or 3' untranslated region of a nucleic acid encoding a Rad51 protein, wherein said antisense molecule comprises a nucleic acid having a sequence selected from the group consisting of AS4 (SEQ ID NO: 5), AS5 (SEQ ID NO: 6), AS6 (SEQ ID NO: 7), AS7 (SEQ ID NO: 8), AS8 (SEQ ID NO: 9) and A59 (SEQ ID NO: 10).

2. A Rad51 antisense molecule having a sequence targeted to the 5' or 3' untranslated region of a nucleic acid encoding a Rad51 protein, wherein said antisense molecule is a nucleic acid selected from the group consisting of AS4 (SEQ ID NO: 5), AS5 (SEQ ID NO: 6), AS6 (SEQ ID NO: 7), AS7 (SEQ ID NO: 8), AS8 (SEQ ID NO: 9) and AS9 (SEQ ID NO: 10).

* * * * *